United States Patent
Awadallah-F et al.

(10) Patent No.: US 11,447,392 B2
(45) Date of Patent: Sep. 20, 2022

(54) CARBON NANOTUBES DECORATED WITH CARBON NANOSPHERES

(71) Applicant: QATAR UNIVERSITY, Doha (QA)

(72) Inventors: Ahmed Awadallah-F, Doha (QA); Shaheen A. Al-Muhtaseb, Doha (QA)

(73) Assignee: QATAR UNIVERSITY, Doha (QA)

(*) Notice: Subject to any disclaimer, the term of this patent is extended or adjusted under 35 U.S.C. 154(b) by 253 days.

(21) Appl. No.: 16/804,212

(22) Filed: Feb. 28, 2020

(65) Prior Publication Data
US 2020/0277193 A1 Sep. 3, 2020

Related U.S. Application Data

(63) Continuation of application No. PCT/IB2019/051690, filed on Mar. 2, 2019.

(51) Int. Cl.
| | |
|---|---|
| *C01B 32/166* | (2017.01) |
| *C01B 32/18* | (2017.01) |
| *C08J 3/075* | (2006.01) |
| *C02F 1/68* | (2006.01) |
| *B01J 21/18* | (2006.01) |
| *B82Y 30/00* | (2011.01) |
| *B82Y 5/00* | (2011.01) |
| *B82Y 40/00* | (2011.01) |

(52) U.S. Cl.
CPC ........ *C01B 32/166* (2017.08); *B01J 21/185* (2013.01); *C01B 32/18* (2017.08); *C02F 1/68* (2013.01); *C08J 3/075* (2013.01); *B82Y 5/00* (2013.01); *B82Y 30/00* (2013.01); *B82Y 40/00* (2013.01); *C01P 2002/74* (2013.01); *C01P 2002/82* (2013.01)

(58) Field of Classification Search
CPC ... C01B 32/166; C01B 32/18; C01B 2202/06; C01B 32/00; C01B 32/174; C01B 32/336; B01J 21/185; C02F 1/68; C02F 1/283; C02F 2305/08; C08J 3/075; B82Y 5/00; B82Y 30/00; B82Y 40/00; C01P 2002/74; C01P 2002/82
See application file for complete search history.

(56) References Cited

U.S. PATENT DOCUMENTS

| | | |
|---|---|---|
| 6,277,766 B1 | 8/2001 | Ayers |
| 2003/0044608 A1 | 3/2003 | Yoshizawa et al. |

(Continued)

FOREIGN PATENT DOCUMENTS

| | | |
|---|---|---|
| EP | 1891230 B1 | 12/2010 |
| WO | WO 2007/067079 A1 | 6/2007 |

(Continued)

OTHER PUBLICATIONS

Song, et al., Fabrication of fullerene-decorated carbon nanotubes and their application in flame-retarding polypropylene, Nanoscale 2009; 1: 118-121 (Year: 2009).*

(Continued)

*Primary Examiner* — Daniel C. McCracken
(74) *Attorney, Agent, or Firm* — Squire Patton Boggs (US) LLP

(57) ABSTRACT

Provided are multiwalled carbon nanotubes (MWCNTs) decorated with nanospheres of carbon, methods of preparing multiwalled carbon nanotubes (MWCNTs) decorated with nanospheres of carbon, and uses thereof.

43 Claims, 6 Drawing Sheets

(56) References Cited

U.S. PATENT DOCUMENTS

| | | |
|---|---|---|
| 2007/0158610 A1 | 7/2007 | Hong et al. |
| 2008/0220244 A1 | 9/2008 | Wai et al. |
| 2009/0072192 A1 | 3/2009 | Seal et al. |
| 2009/0224435 A1 | 9/2009 | Gogotsi et al. |
| 2011/0247866 A1 | 10/2011 | Kim et al. |
| 2012/0077006 A1 | 3/2012 | Worsley et al. |
| 2012/0207938 A1 | 8/2012 | Chen et al. |
| 2012/0261620 A1* | 10/2012 | Richter .................. B82Y 40/00 252/500 |
| 2013/0065050 A1 | 3/2013 | Chen et al. |
| 2014/0377790 A1 | 12/2014 | Ramaprabhu et al. |
| 2016/0045882 A1 | 2/2016 | Coulombe et al. |
| 2017/0275169 A1 | 9/2017 | Galimberti et al. |

FOREIGN PATENT DOCUMENTS

| | | |
|---|---|---|
| WO | WO 2014/189549 A2 | 11/2014 |
| WO | WO 2015/044964 A1 | 4/2015 |

OTHER PUBLICATIONS

Joris, et al., The Effects of Polar Aprotic Solvents on Linear Free-Energy Relationships in Hydrogen-Bonded Complex Formation, Journal of the American Chemical Society 1972; 94(10): 3438-3442 (Year: 1972).*

Zhu, et al., Interconnected carbon nanotube-graphene nanosphere scaffolds as free-standing paper electrode for high-rate and ultra-stable lithium-sulfur batteries, Nano Energy 2015; 11: 746-755 (Year: 2015).*

International search report and written opinion of the PCT/IB2019/051690 dated Jun. 21, 2019; 8 pages.

Barzegar et al., "$C_{60}$/Collapsed Carbon Nanotube Hybrids: A Variant of Peapods", Nano Letters, Jan. 2, 2015, vol. 15, pp. 829-834; DOI: 10.1021/n15033581829.

Qu et al., "Tunable assembly of carbon nanospheres on single-walled carbon nanotubes", Nanotechnology, vol. 21, 2010, 305602 (8pp); doi:10.1088/0957-4484/21/30/305602.

Zhou et al., "Carbon Nanospheres Hung on Carbon Nanotubes: A Hierarchical Three-Dimensional Carbon Nanostructure for High-performance Supercapacitors", Journal of Materials Chemistry A, vol. 32, 2017; 12 pages.

Aghamiri, et al: "Fabrication and characterization of cytochrome c-immobilized polyaniline/multi-walled carbon nanotube composite thin film layers for biosensor applications", Thin Solid Films, Jun. 28, 2018; vol. 660, pp. 484-492.

Ahmadpoor, et al: "Decoration of multi-walled carbon nanotubes with silver nanoparticles and investigation on its colloid stability", Materials Chemistry and Physics 2013; vol. 139, pp. 113-117.

Anas, et al: "Investigation of various aerogels as adsorbents for methane storage", The Journal of Supercritical Fluids, Nov. 29, 2017; vol. 141, pp. 166-172.

Asadzadeh-Khaneghah, et al: "Decoration of carbon dots and AgCl over g-C3N4 nanosheets: Novel photocatalysts with substantially improved activity under visible light", Separation and Purification Technology, Jan. 12, 2018; vol. 199, pp. 64-77.

Awadallah-F, et al: "Nanofeatures of resorcinol-formaldehyde carbon microspheres", Materials Letters Aug. 1, 2012; vol. 87, pp. 31-34.

Baikousi, et al: "Surface decoration of carbon nanosheets with amino-functionalized organosilica nanoparticles", Applied Surface Science, Dec. 11, 2011; vol. 258, pp. 3703-3709.

Berardi, "The benefits of using aerogel-enhanced systems in building retrofits", Procedia Engineering 2017; vol. 134, pp. 626-635; $9^{th}$ International Conference on Sustainability in Energy and Buildings, SEB-17, Jul. 5-7, 2017, Chania, Crete, Greece.

Bi, et al: "New graphene form of nanoporous monolith for excellent energy storage", Nano Letters Dec. 7, 2015; vol. 16, pp. 349-354.

Blaudeck, et al: "Wafer-level decoration of carbon nanotubes in field-effect transistor geometry with performed gold nanoparticles using a microfluidic approach", Microelectronic Engineering, Sep. 26, 2014; vol. 137, pp. 135-140.

Chao, et al: "Large enhancements in hydrogen production of TiO2 through a simple carbon decoration", Carbon, Jun. 5, 2013; vol. 62, pp. 69-75.

Charlier, et al: "Electronic and transport properties of nanotubes", Reviews of Modern Physics, Apr.-Jun. 2007; vol. 79, No. 2, pp. 677-732.

Chen, et al: "Covalently cross-linked graphene oxide aerogel with stable structure for high-efficiency water purification", Chemical Engineering Journal, Aug. 12, 2018; vol. 354, pp. 896-904.

Chen, et al: "Self-assembly of 3D neat porous carbon aerogels with NaCl as template and flux for sodium-ion batteries", Journal of Power Sources, Jun. 9, 2017; vol. 359, pp. 529-538.

Choi, et al: "Dual sensitization of MWCNTs by co-decoration and p- and n-type metal oxide nanoparticles", Sensors and Actuators B 264, pp. 150-163; Feb. 27, 2018.

De Volder, et al: "Carbon nanotubes: present and future commercial applications", Science Feb. 1, 2013; vol. 339, pp. 535-539.

Ding, et al: "Facile decoration of carbon fibers with Ag nanoparticles for adsorption and photocatalytic reduction of CO2", Applied Catalysis B: Environmental 202, pp. 314-325; Sep. 20, 2016.

Dolai, et al: "Carbon-dot-aerogel sensor for aromatic volatile organic compounds", Sensors and Actuators B: Chemical, Oct. 27, 2016; vol. 241, pp. 607-613.

Enayatpour, et al: "Adsorption/desorption study of proteins onto multi-walled carbon nanotubes and amino multi-walled carbon nanotubes surfaces as adsorbents", Journal of Molecular Liquids, Feb. 10, 2017; vol. 231, pp. 566-571.

Evanoff, et al: "Towards ultrathick battery electrodes: aligned carbon nanotube-enabled architecture", Advanced Materials 2012; vol. 24, pp. 533-537.

Feng, et al: "Decoration of carbon cloth by manganese oxides for flexible asymmetric supercapacitors", Ceramics International, Mar. 29, 2017; vol. 43, pp. 8321-8328.

Franklin, et al: "Variability in carbon nanotube transistors: Improving deviceto-device consistency", ACS Nano, Article, Jan. 24, 2012; vol. 6, No. 2, pp. 1109-1115.

Gong, et al: "Tribological properties of polymeric aryl phosphates grafted onto multi-walled carbon nanotubes as high-performance lubricant additive", Tribology International 2017; doi: 10.1016/j.triboint.2017.07.010.

Guan, et al: "Multi-walled carbon nanotubes acting as antioxidant for fluorosilicone rubber", Polymer Degradation and Stability Sep. 11, 2018; vol. 156, pp. 161-169.

Holec, et al: "Theory-guided metal-decoration of nanoporous carbon for hydrogen storage applications", Surface & Coatings Technology, Jul. 26, 2018; vol. 351, pp. 42-49.

Hosseini, et al: "BC/rGO conductive nanocomposite aerogel as a strain sensor", Polymer 2017; doi: 10.1016/j.polymer.2017.12.028; 51 pages.

Hsieh, et al: "Decoration of zinc oxide nanoparticles onto carbon fibers as composite filaments for infrared heaters", Surfaces and Interfaces, Dec. 24, 2016; vol. 6; pp. 98; pp. 102.

Huo, et al: "N-doped graphene/carbon hybrid aerogels for efficient solar steam generation", Carbon 2019; Oct. 4, 2018; vol. 142, pp. 13-19.

Hussain, et al: "Decoration of carbon nanotubes with magnetic Ni1-xCOxFe2O4 nanoparticles by microemulsion method", Journal of Alloys and Compounds, Aug. 7, 2012; vol. 544, pp. 99-104.

Ihsanullah: "Carbon nanotube membranes for water purification: developments, challenges, and prospects for the future", Separation and Purification Technology Jul. 20, 2018; vol. 209, pp. 307-337.

Isa, et al: "Multi-walled carbon nanotubes doped Poly(Methyl MethAcrylate) microfiber for relative humidity sensing", Sensors and Actuators A: Physical, Jan. 31, 2018; vol. 272, pp. 274-280.

Jarrais, et al: "Spontaneous gold decoration of activated carbons", Inorganica Chimica Acta, Jul. 10, 2013; vol. 408, pp. 235-239.

(56) References Cited

OTHER PUBLICATIONS

Jiao, et al: "Preparation and electrochemical performance of hollow activated carbon fiber—Carbon nanotubes three-dimensional self-supported electrode for supercapacitor", Materials and Design, May 12, 2018; vol. 154, pp. 239-245.
Jiang, et al: "Lightweight spongy bone-like graphene@SiC aerogel composites for high-performance microwave absorption", Chemical Engineering Journal, Dec. 27, 2017; vol. 337, pp. 522-531.
Katz, et al: "Biomolecule-functionalized carbon nanotubes: Applications in Nanobioelectronics", Reviews: ChemPhysChem 2004; vol. 5, pp. 1084-1104.
Keshipour, et al: "Cross-linked chitosan aerogel modified with Au: Synthesis, characterization and catalytic application", Carbohydrate Polymers, May 24, 2018; vol. 196, pp. 494-500.
Kim, et al: "The impregnated synthesis of polypyrrole into carbon aerogel and its applications to photovoltaic materials", Synthetic Metals 2004; vol. 142, pp. 153-160.
Kong, et al: "Ex-situ decoration of ordered mesoporous carbon with palladium nanoparticles via polyoxometalates and for sensitive detection of acetaminophen in pharmaceutical products", Journal of Colloid and Interface Science, Jun. 20, 2017; vol. 505, pp. 615.621.
Kong, et al: "High-performing multi-walled carbon nanotubes/silica nanocomposites for elastomer application", Composites Science and Technology, Apr. 7, 2018; vol. 162, pp. 23-32.
Kong, et al: "Switchable dual-wavelength all-fiber laser mode-locked by carbon nanotubes", IOPscience Laser Physics 2015; vol. 25, 6 pages.
Koo, et al: "Decoration of multi-walled carbon nanotubes with FexNi1-x alloys and their magnetic properties", Journal of Alloys and Compounds, Sep. 17, 2016; vol. 693, pp. 1083-1089.
Kumar, et al: "In situ decoration of silver nanoparticles on silver-walled carbon nanotubes by microwave irradiation for enhanced and durable anti-bacterial finishing on cotton fabric", Ceramics International 2018, Article in Press; https://doi.org/10/1016/j.ceramint.2018.09.280.
Kumar, et al: "Potential application of multi-walled carbon nanotubes/activated carbon/bamboo charcoal for efficient alcohol sensing", Journal of Alloys and Compounds, Jun. 15, 2018; vol. 767, pp. 215-222.
Kwok, et al: "Graphene-carbon nanotube composite aerogel with Ru@Pt nanoparticle as a porous electrode for direct methanol microfluidic fuel cell", Applied Energy, Feb. 28, 2018; vol. 217, pp. 258-265.
Lee, et al: "Antimicrobial properties of lignin-decorated thin multi-walled carbon nanotubes in poly(vinyl alcohol) nanocomposites", European Polymer Journal, May 21, 2018; vol. 105, pp. 79-84.
Lee, et al: "Simple and direct synthesis of ZnO decorated multi-walled carbon nanotube for supercapacitor electrodes", Colloids and Surfaces A 2018; Oct. 28, 2017; vol. 538, pp. 23-27.
Lei, et al: "Fabrication of metal-organ ice frameworks@cellulose aerogels composite materials for removal of heavy metal ions in water", Carbohydrate Polymers, Oct. 11, 2018; vol. 205, pp. 35-41.
Li, et al: "Decoration of carbon-supported Pt catalysts with Sn to promote electro-oxidation of ethanol", Journal of Power Sources 2007; vol. 173, pp. 121-129.
Liu, et al: "Catalytic effects of calcium and potassium on a curved char surface in fuel reburning: A first-principles study on the adsorption of nitric oxide on single-wall carbon nanotubes with metal decoration", Energy, Feb. 23, 2017; vol. 125, pp. 459-469.
Liu, et al: "Decoration of carbon nanotubes with chitosan", Carbon, Aug. 1, 2005; vol. 43, pp. 3178-3180.
Lopez-Iglesias, et al: "From the printer to the lungs: Inkjet-printed aerogel particles for pulmonary delivery", Chemical Engineering Journal, Sep. 22, 2018; vol. 357, pp. 559-566.
Lu, et al: "Convenient fabrication of graphene/gold nanoparticle aerogel as direct electrode for H2O2 sensing", Materials Letters, Jul. 8, 2017; vol. 207, pp. 49-52.
Lu, et al: "Effect of surface modifications on the decoration of multi-walled carbon nanotubes with ruthenium nanoparticles", Carbon 2007; vol. 45, pp. 1599-1605.
Luo, et al: "Printing single-walled carbon nanotube/Nafion composites by direct writing techniques", Materials and Design, May 25, 2018; vol. 155, pp. 125-133.
Maleki, et al: "Synthesis and biomedical applications of aerogels: Possibilities and challenges", Advances in Colloid and Interface Science; vol. 236, pp. 1-27.
Martis, et al: "Infrared irradiation controlled decoration of multiwalled carbon nanotubes with copper/copper oxide nanocrystals", Acta Materialia 2011; vol. 59, pp. 5040-5047.
Martis, et al: "Selective decoration of nickel and nickel oxide nanocrystals on multiwalled carbon nanotubes", Journal of Solid State Chemistry, Mar. 23, 2011; vol. 184, pp. 1245-1250.
Mccafferty, et al: "Decoration of multiwalled carbon nanotubes with protected iron nanoparticles", Carbon, Nov. 26, 2014; vol. 84, pp. 47-55.
Mccarthy, et al: "Low-voltage, low-power, organic light-emitting transistors for active matrix displays", Science, Mar. 10, 2011; vol. 332, pp. 569-573.
Mcenaney, et al: "Aerogel-based solar thermal receivers", Nano Energy, Aug. 9, 2017; vol. 40, pp. 180-186.
Mohajeri, et al: "Li-decoration on the edge oxidized graphyne and graphdiyne: A first principles study", Computational Materials Science, Feb. 2, 2016; vol. 115, pp. 51-59.
Mohajeri, et al: "Light metal decoration on nitrogen/sulfur codoped graphyne: An efficient strategy for designing hydrogen storage media", Physica E: Low-dimensional Systems and Nanostructures, Apr. 7, 2018; vol. 101, pp. 167-173.
Moreno, et al: "Decoration of multi-walled carbon nanotubes with metal nanoparticles in supercritical carbon dioxide medium as a novel approach for the modification of screen-printed electrodes", Talanta, Sep. 17, 2016; vol. 161, pp. 775-779.
Mousave, et al: "Decoration of Fe3O4 and CoWO4 nanoparticles over graphitic carbon nitride: Novel visible-light-responsive photocatalysts with exceptional photocatalytic performances", Materials Research Bulletin, Apr. 30, 2018; vol. 105, pp. 159-171.
Muratore, et al: "Nanoparticle decoration of carbon nanotubes by sputtering", Carbon, Feb. 1, 2013; vol. 57, pp. 274-281.
Nie, et al: "Sensitivity enhanced, stability improved ethanol gas sensor based on multi-wall carbon nanotubes functionalized with Pt-Pd nanoparticles", Sensors and Actuators B: Chemical Apr. 30, 2018; vol. 270, pp. 140-148.
Oschatz, et al: "Carbide-derived carbon aerogels with tunable pore structure as versatile electrode material in high power supercapacitors", Carbon 2017; Nov. 19, 2016; vol. 113, pp. 283-291.
Parveen, et al: "Decoration of zinc oxide nanoparticles on vertically aligned single wall carbon nanotubes: An efficient field emitter", Materials Research Bulletin, May 3, 2016; vol. 83, pp. 12-18.
Peng, et al: "Measurements of near-ultimate strength for multiwalled carbon nanotubes and irradiation-induced crosslinking improvements", Nature Nanotechnology, Articles Oct. 2008; published online Aug. 10, 2008; vol. 3, pp. 626-631.
Perez-Caballero, et al: "Preparation of nanostructured carbon materials", Proceedings of the Estonian Academy of Sciences 2008, vol. 57, No. 1, pp. 48-53.
Rad, et al: "How can nickel decoration affect H2 adsorption on B12P12 nano-heterostructures?", Journal of Molecular Liquids, Feb. 4, 2018; vol. 255, pp. 168-175.
Rahimabady, et al: "Dielectric nanocomposite of diphenylethylenediamine and P-type multi-walled carbon nanotube for capacitive carbon dioxide sensors", Sensors and Actuators B: Chemical 2017, Dec. 8, 2016; vol. 243, pp. 596-601.
Reddy, et al: "Hydrogen storage properties of nanocrystalline Pt dispersed multi-walled carbon nanotubes", International Journal of Hydrogen Energy Jun. 27, 2007; vol. 32, pp. 3998-4004.
Ribeiro, et al: "Palladium decoration of hybrid carbon nanotubes/charcoal composite and its catalytic behavior in the hydrogenation of trans-cinnamaldehyde". Journal of Molecular Catalysis A: Chemical, Sep. 2, 2015; vol. 410, pp. 34-40.
Salem, et al: "Facile decoration of TiO2 nanoparticles on graphene for solar degradation of orgranic dye", Solid State Sciences, Sep. 19, 2016; vol. 61, pp. 131-135.

(56) References Cited

OTHER PUBLICATIONS

Salice, et al: "An insight into the functionalisation of carbon nanotubes by diazonium chemistry: Towards a controlled decoration", Carbon, Mar. 7, 2014; vol. 74, pp. 73-82.
Samuel, et al: "Decoration of MnO nanocrystals on flexible free-standing carbon nanofibers for lithium ion battery anodes", Electrochimica, Feb. 16, 2017; vol. 231, pp. 582-589.
Sarapuu, et al: "Electrocatalysis of oxygen reduction by iron-containing nitrogen-doped carbon aerogels in alkaline solution", Electrochimica Acta, Jan. 25, 2017; vol. 230, pp. 81-88.
Shameli, et al: "Synthesis of cross-linked PVA membranes embedded with multi-wall carbon nanotubes and their application to esterification of acetic acid with methanol", Chemical Engineering Journal Oct. 11, 2016; vol. 309, pp. 381-396.
Shengguo, et al: "Outstanding superhydrophobicity and corrosion resistance on carbon-based film surfaces coupled with multiwalled carbon nanotubes and nickel nanoparticles", Surface Science Jul. 20, 2018; vol. 677, pp. 193-202.
Shi, et al: "Carbon nanotube decorated with silver nanoparticles via noncovalent interaction for a novel nonenzymatic sensor towards hydrogen peroxide reduction", Journal of Electroanalytical Chemistry, Mar. 1, 2011; vol. 656, pp. 29-33.
Shi, et al: "Tailoring catalytic performance of carbon nanotubes confined CuO—CeO2 catalysts for CO preferential oxidation", International Journal of Hydrogen Energy Aug. 29, 2018; vol. 43, pp. 18211-18219.
Shivakumar, et al: "ICNANO 2016: Decoration of copper nanoparticles on multiwalled carbon nanotubes and the study of electrocatalytic activity for methanol oxidation", Materials Today 2017, Proceedings 4; 12012-12020.
Shouman, et al: "Microporous nanohybrids of carbon xerogels and multi-walled carbon nanotubes for removal of rhodamine B dye", Journal of Water Process Engineering Apr. 6, 2018; vol. 23, pp. 165-173.
Singh, et al: "Facile synthesis of highly conducting and mesoporous carbon aerogel as platinum support for PEM fuel cells", International Journal of Hydrogen Energy, Mar. 22, 2017; vol. 42, pp. 11110-11117.
Sinha, et al: "Ultrananocrystalline diamond decoration on to the single wall carbon nano tubes", Applied Surface Science, Dec. 24, 2016; vol. 418, pp. 401-405.
Stobinski, et al: "Decoration of carboxylated multi-wall carbon nanotubes with quantum dots", Journal of Alloys and Compounds 2008; vol. 455, pp. 137-141.
Sun, et al: "Preparation of Ni/CNTs catalyst with high reducibility and their superior performance in benzene hydrogenation", Applied Catalysis A: General May 11, 2016; vol. 522; vol. 180-187.
Sun, et al: "Ultrasonication-assisted uniform decoration of carbon nanotubes by various particles with controlled size and loading", Carbon, Jun. 13, 2011; vol. 49, pp. 4376-4384.
Tan, et al: "Fine decoration of carbon nanotubes with metal organic frameworks for enhanced performance in supercapacitance and oxygen reduction reaction", Science Bulletin, Aug. 10, 2017; vol. 62, pp. 1132-1141.
Terasawa, et al: Proceedings of the International Conference on Diamond and Carbon Materials "Electrochemical and electromechanical properties of activated multi-walled carbon nanotube polymer actuator that surpass the performance of a single-walled carbon nanotube polymer actuator", Materials Today: Proceedings 3S 2016; S178-S183.
Tsai, et al: "Enhancing hydrogen storage on carbon nanotubes via hybrid chemical etching and Pt decoration employing supercritical carbon dioxide fluid", International Journal of Hydrogen Energy, Feb. 2, 2012; vol. 37, pp. 6714-6720.
Ullah, et al: "Decoration of graphite nanoplatelets with Nb2O5 deposited by radio frequency sputtering", Diamond & Related Materials, Sep. 7, 2018; vol. 89, pp. 206-217.
Urper, et al: "Fabrication of carbon nanotube transparent conductive films by vacuum filtration method", Materials Letters, Mar. 29, 2018; vol. 223, pp. 210-214.

Vellingiri, et al: "Characterization and hydrogen storage properties of SnO2 functionalized MWCNT nanocomposites", Interational Journal of Hydrogen Energy 2018; vol. 43, pp. 10396-10409.
Vivo-Vilches, et al: "From carbon molecular sieves to VOCs filters: Carbon gels with tailored porosity for hexane isomers adsorption and separation", Microporous and Mesoporous Materials, May 18, 2018; vol. 270, pp. 161-167.
Wan, et al: "Graphene oxide/cellulose aerogels nanocomposite: Preparation, pyrolysis, and application for electromagnetic interference shielding", Carbohydrate Polymers, May 18, 2016; vol. 150, pp. 172-179.
Wang, et al: "3D carbon quantum dots/graphene aerogel as a metal-free catalyst for enhanced photosensitization efficiency", Applied Catalysis B: Environmental, Mar. 30, 2018; vol. 233, pp. 11-18.
Wang, et al: "Preparation of carbon nanotubes/graphene hybrid aerogel and its application for the adsorption of organic compounds", Carbon, Apr. 3, 2017; vol. 118, pp. 765-771.
Wang, et al: "Removal of organic solvents/oils using carbon aerogels derived from waste durian shell", Journal of the Taiwan Institute of Chemical Engineers, Jul. 4, 2017; vol. 78, pp. 351-358.
Wen, et al: "Decoration of carbon nanotubes with highly dispersed platinum nanoparticles for electrocatalytic application", Journal of Electroanalytical Chemistry, Nov. 28, 2014; vol. 738, pp. 77-83.
White, et al: "Characterisation of commercially CVD grown multi-walled carbon nanotubes for paint applications", Progress in Organic Coatings, Oct. 22, 2015; vol. 90, pp. 44-53.
Wu, et al: "Self-imaging in multi-walled carbon nanotube arrays at visible wavelengths", Carbon, Jul. 2, 2016; vol. 108, pp. 47-51.
Xie, et al: "ZnO nanowires decoration on carbon fiber via hydrothermal synthesis for paper-based friction materials with improved friction and wear properties", Ceramics International, Dec. 2017; vol. 44, pp. 4204-4210.
Xiong, et al: "Multi-walled carbon nanotube/amino-functionalized MIL-53(Fe) composites: Remarkable adsorptive removal of antibiotics from aqeous solutions", Chemosphere Jul. 18, 2018; vol. 210, pp. 1061-1069.
Xu, et al: "Carbon aerogel-based supercapacitors modified by hummers oxidation method", Journal of Colloid and Interface Science, May 14, 2018; vol. 527, pp. 25-32.
Xu, et al: "DFT study of nanotubes as the drug delivery vehicles of Efavirenz", Computational and Theoretical Chemistry, Mar. 31, 2018; vol. 1131, pp. 57-68.
Xu, et al: "Lignin-based carbon fibers: Carbon nanotube decoration and superior thermal stability", Carbon, Aug. 23, 2014; vol. 80, pp. 91-102.
Xu, et al: "Self-healing thermoplastic polyurethane (TPU)/polycaprolactone (PCL)/multi-wall carbon nanotubes (MWCNTs) blend as shape-memory composites", Composites Science and Technology, Oct. 10, 2018; vol. 168, pp. 255-262.
Yahya, et al: "MWCNT for ambient urea synthesis", Physica B: Condensed Matter 2018; vol. 545, pp. 358-369.
Yang, et al: "Activated carbon aerogels with developed mesoporosity as high-rate anodes in lithium-ion batteries", Journal of Materials Science; Mar. 4, 2016; vol. 51, pp. 5565-5571.
Yang, et al: "Modelling and optimization of the pore structure of carbon aerogels using an artificial neural network", Mew Carbon Materials, Feb. 2017; vol. 32, Issue 1, pp. 77-85.
Yao, et al: "In situ surface decoration of Fe3C/Fe3O4/C nanosheets: Towards bi-functional activated carbons with supercapacitance and efficient dye adsorption", Bioresource Technology, Feb. 6, 2018; vol. 256, pp. 208-215.
Ye, et al: "Decorating catalytic palladium nanoparticles on carbon nanotubes in supercritical carbon dioxide", Chemical Communication, Feb. 10, 2003; The Royal Society of Chemistry 2003, pp. 642-643.
Yu, et al: "Polypyrrole-anchored cattail biomass-derived carbon aerogels for high performance binder-free supercapacitors", Carbohydrate Polymers, Apr. 18, 2018; vol. 199, pp. 555-562.
Yue, et al: "Hybrid aerogels derived from banana peel and waste paper for efficient oil adsorption and emulsion separation", Journal of Clearner Production, Jul. 20, 2018; vol. 199, pp. 411-419.
Zhang, et al: "Beryllium and boron decoration form planar tetracoordinate carbon strips at the edge of BCN nanoribbons result

(56) References Cited

OTHER PUBLICATIONS in energy gap opposite variation and third-order nonlinear optical response improvement", Chemical Physics Letters, Aug. 1, 2017; vol. 685, pp. 4322-4437.

Zhang, et al: "Synthesis of Ag decoration on carbon coated Zn2GeO4 nanorods and its enhanced properties as anode materials for lithium-ion batteries", Materials Letters, Dec. 23, 2015; vol. 166, pp. 243-246.

Zhang, et al: "Synthesis of core-shell covalent organic frameworks/multi-walled carbon nanotubes nanocomposite and application in lithium-sulfur batteries", Materials Letters, Nov. 2, 2017; vol. 213, pp. 143-147.

Zhao, et al: "Diamond-like carbon decoration enhances the field electron emission of silicon nanowires", Surface & Coatings Technology, Jun. 2, 2012; vol. 228, pp. S349-S353.

Zhao, et al: "Electroless decoration of cellulose paper with nickel nanoparticles: A hybrid carbon fiber for supercapacitors", Materials Chemistry and Physics, May 16, 2018; vol. 215, pp. 157-162.

Zhao, et al: "PEGylated multi-walled carbon nanotubes as versatile vector for tumor-specific intracellular triggered release with enhanced anti-cancer efficiency: Optimization of length and PEGylation degree", Colloids and Surfaces B: Biointerfaces, Feb. 20, 2018; vol. 168, pp. 43-49.

Zheng, et al: "Global transcriptional responses of denitrifying bacteria to functionalized single-walled carbon nanotubes revealed by weighted gene-coexpression network analysis", Science of the Total Environment, Sep. 2, 2017; vols. 613-614, pp. 1240-1249.

Zhong, et al: "Fabrication of Pt-doped carbon aerogels for hydrogen storage by radiation method", International Journal of Hydrogen Energy, Sep. 18, 2018, vol. 43, pp. 19174-19181.

Zhu, et al: "Clay-based nanofibrous membranes reinforced by multi-walled carbon nanotubes", Ceramics International Jun. 6, 2018; vol. 44, pp. 15873-15879.

Zhu, et al: "Design and optimization of core/shell structures as highly efficient opacifiers for silica aerogels as high-temperature thermal insulation", International Journal of Thermal Sciences, Jul. 29, 2018; vol. 133, pp. 206-215.

Zuo, et al: "Enhanced field emission and hysteresis characteristics of aligned carbon nanotubes with Ti decoration", Organic Electronics, Jun. 4, 2013; vol. 14, pp. 2306-2314.

A. Awadallah-F et al., "Carbon NanoParticles-Decorated Carbon Nanotubes", Scientific Reports, www.nature.com/Scientific Reports, (2020) 10:4878, https://doi.org/10.1038/s41598-020-61726-4, natureresearch, 7 pages.

M. Pedrosa et al., "Chemical Surface Modification and Characterization of Carbon nanostructures Without Shape Damage", Materials Research, 2020; 23(2): e20190493, DOI:https://doi.org/10.1590/1080-5373-MR-2019-0493, 8 pages.

N. Furuuchi et al., "Self-Assembled Fullerene Crystals as Excellent Aromatic Vapor Sensors", Sensors 2019, 19, 267; doi: 10.3390/s19020267,12 pages, www.mdpi.com/journal/sensors.

S. Zhang et al., "Effect of Self-Assembly of Fullerene Nano-Particles on Lipid Membrane", Published Oct. 29, 2013, https://doi.org/10.1371/journal.pone.0077436, 13 pages.

Wenjie Nie et al., "Interaction between multi-walled carbon nanotubes and propranolol", Scientific Reports (2020) 10:01259, https://doi.org/10.1038/s41598-020-66933-7, nature research, 9 pages.

P. Kalyani et al., "Refuse Derived Energy—Tea Derived Boric Acid Activated Carbon as an Electrode Material for Electrochemical Capacitors", Portugaliae Electrochimica Acta 2013, 31(3), 165-174, DOI:10.4152/pea.201303165, 10 pages.

Abdelghaffar Nasri et al., "High-Sensitivity Sensor Using C60-Single Molecule Transistor", IEEE Sensors Journal, vol. 18, No. 1, Jan. 1, 2018, DOI: 10.1109/JSEN.2017.2769803, 7 pages.

Saba Goodarzi et al., "Fullerene: biomedical engineers get to revisit an old friend", Materials Today, vol. 20, No. 8, Oct. 2017, Elsevier, http://dx.doi.org/10.1016/j.mattod.2017.03.017, 21 pages.

Ahmed I. Osman et al., "Production and characterisation of activated carbon and carbon nanotubes from potato peel waste and their application in heavy metal removal", Environmental Science and Pollution Research (2019) 26:37228-37241, https://doi.org/10.1007/s11356-019-06594-w, 14 pages.

Bingzhe Wang et al., "Fabricaton of C60 Fullerene Nanofibers by Volatile Diffusion Method", Hindawi Publishing Corporation, Journal of Nanomaterials, vol. 2013, Article ID 646040, 5 pages, http://dx.doi.org/10.1155/2013/646040, 6 pages.

W. H. Powell et al., "Nomenclature for the C60-Ih and C70-D5h(6) Fullerenes" (IUPAC Recommendations 2002), Pure Appl. Chem., vol. 74, No. 4, pp. 629-695, 2002, International Union of Pure and Applied Chemistry, Organic and Biomolecular chemistry Division Commission on Nomenclature of Organic Chemistry, 67 pages.

Yang Li et al., "Superior CO2, CH4, and H2 uptakes over ultrahigh-surface-area carbon spheres prepared from sustainable biomass-derived char by CO2 activation", Carbon 105 (2016) 454-462, www.elsevier.com/locate/carbon, http://dx.doi.org/10.1016/j.carbon.2016.04.036, 9 pages.

Chada, Nagaraju; Romanos, Jimmy; Hilton, Ramsey; Suppes, Galen; Burress, Jacob; Pfeifer, Peter; Abstract submitted for the Mar. 12 Meeting of the American Physical Society Physical Society. 57(1): W33.012. Bibcode:2012APS.MARW33012C, 1 page.

Soo, Yuchoong; Ghada, Nagaraju; Beckner, Matthew; Romanos, Jimmy; Burress, Jacob; Pfeifer, Peter; Abstract submitted for the Mar. 13 Meeting of the American Physical Society (Mar. 20, 2013), "Adsorbed Methane Film Properties in Nanoporous Carbon Monoliths", Bulletin of the American Physical Society, 58(1): M38.001. Bibcode:2013APS.MARM38001S, 1 page.

D. Lozano-Castello et al., "Activated carbon monoliths for methane storage: influence of binder", Pergamon, Carbon 40 (2002) 2817-2825, PII: S0008-6223(02)00194-X, 9 pages.

\* cited by examiner

CARBON NANOTUBES DECORATED WITH CARBON NANOSPHERES

FIELD

This invention relates generally to the field of nanotechnology and concerns carbon nanosphere-decorated carbon nanotubes.

BACKGROUND

Carbon nanotubes (CNTs) have unique features, such as high mechanical strength, electrical and thermal conductivity, high chemical stability, and large surface area to volume ratios. They could be useful for various applications including catalytic processes, water purification, drug delivery, gene transfer, transparent conducting films and electrochemical analysis.

Previously CNTs have been decorated with either organic compounds or metallic nanoparticles. Decorated carbons reported in literature or available in markets are composites (or complexes) prepared from carbon and metal ions. Regardless of the method of inserting metal ions into a matrix of carbon materials, the insertion of metal ions is often mediated by complex formation.

Carbon aerogels (CA), or carbon nanogels, are ultralight and porous, have electric double-layer properties, and low thermal conductivity. Carbon aerogels could be used in catalysis, catalysis support, ion separations, supercapacitors, and battery materials.

There is a need in the field for improved materials that combine the properties of carbon nanotubes and carbon aerogels. Nano-carbon decoration, based on decorating carbon by carbon has not been described in literature.

BRIEF DESCRIPTION OF THE DRAWINGS

FIG. 1(a) refers to pristine MWCNTs and pristine RFA-CNs, and FIG. 1 (b) refers to hybrid MWCNTs/RFA-CNs decorated with a 1:1 mass ratio at different times for the decoration process (i.e., samples at time zero days (0D), 185 days (185D) and 415 days (415D)).

FIG. 4 (c, d) shows scanning electron microscopy (SEM) of hybrid MWCNTs/RFA-CNs sample 0D. FIG. 4 (e, f) shows scanning electron microscopy (SEM) of hybrid MWCNTs/RFA-CNs sample 185D. FIG. 4 (g, h) shows scanning electron microscopy (SEM) of hybrid MWCNTs/RFA-CNs sample 415D.

FIG. 5(c, d) shows TEM photomicrographs of hybrid MWCNTs/RFA-CNs sample 0D. FIG. 5(e, f) shows TEM photomicrographs of hybrid MWCNTs/RFA-CNs sample 185D. FIG. 5(g, h) shows TEM photomicrographs of hybrid MWCNTs/RFA-CNs sample 415D.

SUMMARY

Figure 1:
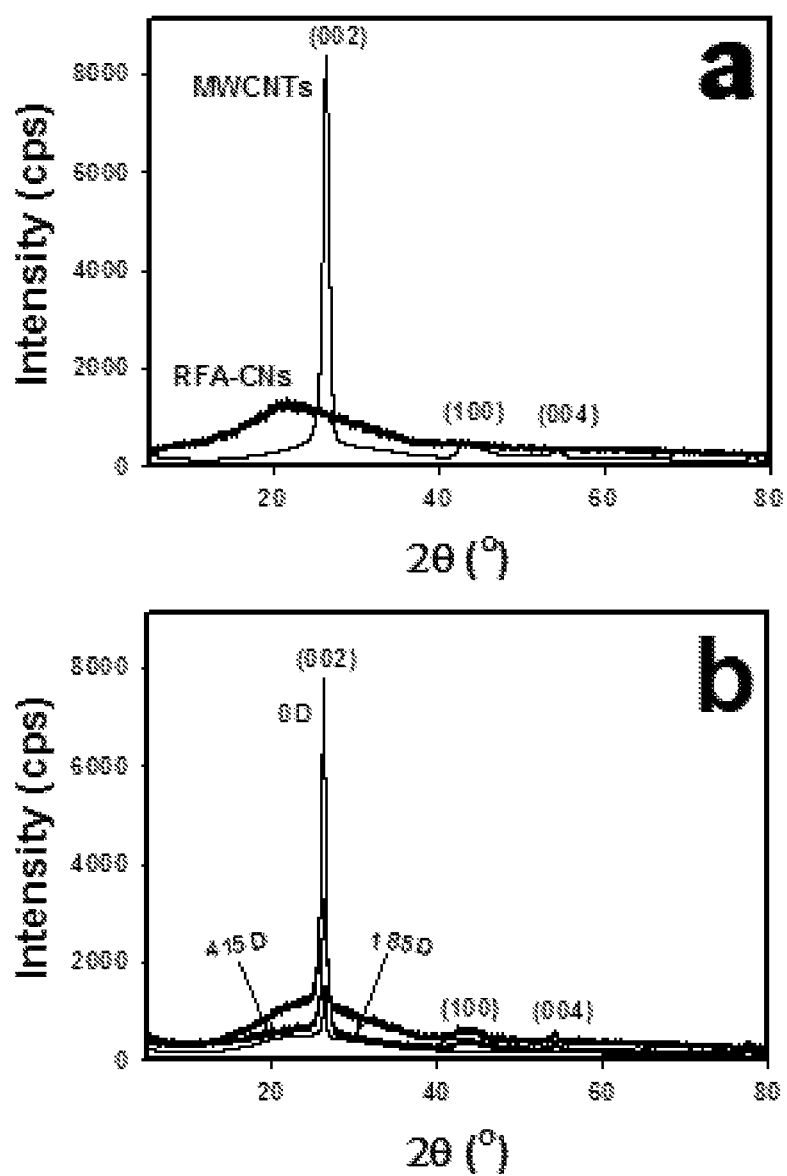
FIG. 1 shows the characteristics of multiwalled carbon nanotubes (MWCNTs) decorated with resorcinol formaldehyde aerogel carbon nanospheres (RFA-CNs) via X-ray diffraction (XRD).

In one aspect, provided herein is a process for preparing a carbon nanotube in contact with an aerogel carbon nanosphere, the process comprising:
(i) providing a mixture comprising aerogel carbon nanospheres and carbon nanotubes in a solvent;
(ii) refluxing the mixture;
(iii) removing the solvent to obtain a carbon nanotube in contact with an aerogel carbon nanosphere.

In another aspect, provided herein is a composition comprising carbon nanotubes in contact with aerogel carbon nanospheres. In a further aspect, provided herein is a composition comprising carbon nanotubes in contact with aerogel carbon nanospheres, where the carbon nanotubes in contact with aerogel carbon nanospheres are prepared by a process described herein in the detailed description section and/or the Examples section.

Also provided herein are methods for preparing carbonized resorcinol-formaldehyde aerogels which can be decorated onto carbon nanotubes.

The features and advantages of the invention will be more readily understood from the following detailed description which should be read in conjunction with the accompanying drawings.

DETAILED DESCRIPTION

Described herein are methods for decorating a first carbon form with a second carbon form different in shape from the first carbon form. As used herein "decorate" means contacting, adhering, annealing, impregnating, or any other non-covalent bonding method of contacting the first carbon form with the second carbon form. Described herein are activated resorcinol/formaldehyde aerogel carbon nanospheres (RFA-CNs) decorating multiwalled carbon nanotubes (MWCNTs).

Definitions

"Carbon nanotubes" refers to allotropes of carbon with a cylindrical nanostructure.

"Aerogel" or "carbon aerogel" refers to a synthetic material derived from a gel, in which the liquid component for the gel has been replaced with a gas, rendering the material porous and light. A carbon aerogel consists primarily of porous carbon.

"Nanosphere," "Nanospherical," or "Nanosphere-dimensioned" refers to spherical material (e.g., particles) with a nanometer diameter e.g., diameters ranging from 1 nm to about 100 nm.

"Resorcinol-formaldehyde aerogel carbon nanosphere" refers to powdered or otherwise solid nanosphere-dimensioned resorcinol-formaldehyde aerogels. The resorcinol-formaldehyde aerogels are formed by the reaction of resorcinol with formaldehyde to form a gel, then replacing the solvent in the gel with a gas (e.g., carbon dioxide gas).

"Room temperature" refers to ambient temperature, and depending on location, may range from about 18° C. to about 35° C. Room temperature is understood to mean 25° C. unless stated otherwise explicitly.

"Solvent exchange" refers to a technique of washing out or substituting a first solvent (e.g., from a gel) and replacing it with a second solvent. Solvent exchange is typically accomplished by adding an excess of a second solvent to a mixture comprising the first solvent, then removing (e.g., decanting) the excess solvents from the mixture and repeating the process till the first solvent is substantially (e.g., more than 50%) replaced by the second solvent.

"Organic solvent" refers to any carbon-hydrogen based solvent. Examples of organic solvents include and are not limited to methanol, ethanol, isopropanol, acetone, tetrahydrofuran, benzene, toluene, acetonitrile, dichloromethane, and the like.

As used herein, the term "about," when qualifying a number, e.g., about 15% w/w, refers to the number qualified and optionally the numbers included in a range about that qualified number that includes ±10% of the number. For example, "about 75° C.," includes 75° C. as well 68° C., 69° C., 70° C., 71° C., 72° C., 73° C., 74° C., 75° C., 76° C., 77° C., 78° C., 79° C., 80° C., 81° C., 82° C., or 83° C.

Processes

In a first aspect, provided herein is a process for preparing a carbon nanotube in contact with a carbon nanosphere, the process comprising:
(i) providing a mixture comprising carbon nanospheres and carbon nanotubes in a solvent;
(ii) refluxing the mixture;
(iii) removing the solvent to obtain a carbon nanotube in contact with an carbon nanosphere.

In some instances, described herein is a process for preparing a carbon nanotube in contact with a carbon nanosphere, the process comprising:
(ia) providing a mixture of carbon nanospheres and carbon nanotubes;
(iib) stirring the mixture of carbon nanospheres and carbon nanotubes in a solvent;
(iiic) refluxing the mixture;
(ivd) removing the solvent and drying the residue to obtain carbon nanotubes with carbon nanospheres disposed thereon.

In a group of embodiments, the carbon nanospheres and the carbon nanotubes are mixed in a dry weight ratio of about 1:1 and stirred in the solvent.

In some instances, the solvent is a protic solvent (e.g., an alcohol). In some instances the solvent is methanol, ethanol or isopropanol. In some instances, the solvent is methanol. In other instances, the solvent is ethanol. In other instances, the solvent is isopropanol.

In some embodiments of the process, the mixture in step (iii) is refluxed for a period of about 1 day-500. In some embodiments of the process, the mixture in step (iii) is refluxed for a period of about 185 days. In some embodiments of the process, the mixture in step (iii) is refluxed for a period of about 1 day-400 days. In some embodiments of the process, the mixture in step (iii) is refluxed for a period of about 1 day-300 days. In some embodiments of the process, the mixture in step (iii) is refluxed for a period of about 1 day-200 days. In some embodiments of the process, the mixture in step (iii) is refluxed for a period of about 1 day-100 days. In some embodiments of the process, the mixture in step (iii) is refluxed for a period of about 400 days-500 days. In some embodiments of the process, the mixture in step (iii) is refluxed for a period of about 300 days-500 days. In some embodiments of the process, the mixture in step (iii) is refluxed for a period of about 200 days-500 days. In some embodiments of the process, the mixture in step (iii) is refluxed for a period of about 100 days-500 days. In some embodiments of the process, the mixture in step (iii) is refluxed for a period of about 415 days. In some embodiments the refluxing is conducted in a sealed system.

In a group of embodiments, the reflux temperature is about 75° C.-125. In a group of embodiments, the reflux temperature is about 100° C. In other instances, the reflux temperature is any suitable temperature based on the solvent being used in the mixture and may be at least the boiling point of the solvent or higher.

In some instances, the residue of step (iv) is dried for a period of about 1 day-5. In some instances, the residue of step (iv) is dried for a period of about 3 days. In some instances, the residue of step (iv) is dried for a period of about 5 days-15 days. In further instances, the residue of step (iv) is dried for any suitable length of time so as in order to obtain carbon nanotubes decorated with carbon nanospheres with low moisture and/or solvent content.

In some instances, the carbon nanotubes are multiwalled carbon nanotubes. In some instances, the multiwalled carbon nanotubes have lengths ranging from 1 μm to 1 cm. In some instances, the multiwalled carbon nanotubes have widths ranging from 1 μm to 1 cm. In some instances, the multiwalled carbon nanotubes have thickness ranging from 0.5 nm to 500 nm in width. In some instances, the multiwalled carbon nanotubes have.

In a group of embodiments, the carbon nanosphere is a resorcinol-formaldehyde aerogel carbon nanosphere, (e.g., a resorcinol-formaldehyde aerogel which is carbonized and/or activated).

In some instances, provided herein is a process wherein the resorcinol-formaldehyde aerogel carbon nanosphere is prepared by a process comprising carbonizing and activating resorcinol-formaldehyde aerogels.

In some instances, provided herein is a process for preparing resorcinol-formaldehyde aerogel carbon nanospheres, the process comprising
a) preparing a resorcinol-formaldehyde aerogel in a solvent and drying said resorcinol-formaldehyde aerogel; and
b) carbonizing and activating the dried resorcinol-formaldehyde aerogel to obtain resorcinol-formaldehyde aerogel carbon nanospheres.

In some instances of the process, the resorcinol-formaldehyde aerogel is prepared by a process comprising:
(iv) providing a mixture comprising resorcinol, a catalyst, formaldehyde, and water;
(v) adjusting the pH to about 7;
(vi) heating the mixture in sealed vials to about 70° C.;
(vii) adding acetic acid to the mixture; and
(viii) heating the sealed vials for about 7 days.

In some other instances of the process, the resorcinol-formaldehyde aerogel is prepared by a process comprising:
(ie) mixing resorcinol and a catalyst in water;
(iif) adding formaldehyde to the mixture of step (i) and adjusting the pH to about 7;
(iiig) transferring the mixture of step (ii) to vials, sealing the vials and heating the sealed vials at about 70° C.;
(ivh) up on solidification of the mixture in each vial of step (iii), adding acetic acid onto the gel surface in each vial and re-sealing each vial;
(vj) continuing to heat the sealed vials of step (iv) for about 7 days to obtain cured gels.

In some instances, the vials are propylene vials. In other instances the vials are glass vials.

In a group of embodiments, the acetic acid is 2% acetic acid. In other instances, the acetic acid is 4%, 6%, 8% or 10% acetic acid. In some instances, the acetic acid is glacial acetic acid.

In some instances the catalyst is an inorganic carbonate. In some instances, the catalyst is sodium carbonate, potassium carbonate, or cesium carbonate, or a combination thereof. In a specific instance, the catalyst is sodium carbonate.

In any of the embodiments described above for the preparation of the resorcinol-formaldehyde aerogel, the pH of about 7 is obtained by addition of an acid and a base. In some of such instances, the pH of about 7 is obtained by addition of nitric acid and ammonium hydroxide.

In some instances, the processes herein comprises
(ix) decanting any excess solution in the vial which is on top of the resorcinol-formaldehyde aerogel; and
(x) solvent exchanging with an organic solvent at room temperature for about 24 hours to produce a cured gel.

In the process for synthesis of the resorcinol-formaldehyde aerogel described above, the process comprises, in some instances, the further steps of
(a) cooling the vials of step (b) and decanting the excess solution on top of the formed gel from each vial;
(c) conducting a solvent exchange with an organic solvent at room temperature by adding the organic solvent on top of the formed gel of step (vi) and maintaining the vials at room temperature for 24 hours;
(d) repeating step (c) two times, for a solvent exchange over a total period of 3 days.

In some instances the organic solvent is an aprotic water miscible solvent. In some instances, the organic solvent is acetone or tetrahydrofuran. In other instances, the organic solvent is dimethyl formamide (DMF), dimethylsulfoxide (DMSO), or acetonitrile (ACN). In a specific instance, the organic solvent is acetone.

In some instances, the process comprises flowing liquid or supercritical carbon dioxide through the cured gel.

In some cases, the process described above for the preparation of the resorcinol-formaldehyde aerogel further comprises the steps of
(e) placing the cured gel in an extractor under liquid carbon dioxide; then depressurizing the extractor and letting the liquid carbon dioxide flow through the gel;
(f) increasing the temperature of the extractor in step (e), and maintaining the extractor at said temperature for at least 2 hours; and
(g) depressurizing the extractor to atmospheric pressure and retrieving the dried resorcinol-formaldehyde aerogel.

In a group of embodiments, the cured gel which is placed in an extractor under liquid carbon dioxide is at a pressure ranging from 1 to 10 MPa and a temperature ranging from about 15° C. to about 25° C. In a group of embodiments, the cured gel which is placed in an extractor under liquid carbon dioxide is at a pressure of 5 MPa and a temperature of 20° C.

In a group of embodiments, the extractor is depressurized to about 1.2 MPa.

In a group of embodiments, after depressurizing, the liquid carbon dioxide is allowed to flow through the gel at a temperature of 20° C. for a time ranging from about 1 to 2.5 hours. In a group of embodiments, after depressurizing, the liquid carbon dioxide is allowed to flow through the gel at 20° C. for a time of 2 hours.

In certain instances, the temperature of the extractor is increased to a temperature of 25° C., and the pressure in the extractor is raised to 5 MPa. In some of such instances, the extractor is maintained at the temperature of 25° C. and the pressure of 5 MPa for at least 2 hours.

In some instances, the carbonizing and activating of the dried resorcinol-formaldehyde aerogel comprises the steps of
(xi) heating the sample of dried resorcinol-formaldehyde aerogel of step (xi) in a furnace for a period of at least 1 hour; and
(xii) cooling the sample to room temperature under carbon dioxide gas flow to obtain resorcinol-formaldehyde aerogel carbon nanospheres.

In some instances, after complete purging of air with nitrogen, the heating of the dried resorcinol-formaldehyde aerogel is conducted at a rate of about 5-15° C./min In some instances, after complete purging of air with nitrogen, the heating of the dried resorcinol-formaldehyde aerogel is conducted at a rate of about 10° C./min up to a temperature of about 600° C.-1000° C., where the furnace has a carbon dioxide gas flow rate of about 100-250 cm$^3$/min, and maintaining the sample at the said temperature. In some instances, the heating of the dried resorcinol-formaldehyde aerogel is conducted at a rate of 10° C./min up to a temperature of 700° C., where the furnace has a carbon dioxide gas flow rate of about 150 cm$^3$/min, and maintaining the sample at the said temperature.

In some instances, after complete purging of air with nitrogen, the heating of the dried resorcinol-formaldehyde aerogel is conducted at a rate of about 5-15° C./min In some instances, after complete purging of air with nitrogen, the heating of the dried resorcinol-formaldehyde aerogel is conducted at a rate of about 10° C./min up to a temperature of 500° C., where the furnace has a nitrogen gas flow rate of about 100 cm$^3$/min, maintaining the sample at the said temperature for 3 hours, and cooling to room temperature while flowing nitrogen to produce carbonized gel. In some instances, the heating of the carbonized gel is conducted at a rate of 10° C./min up to a temperature of 700° C., where the furnace has a carbon dioxide gas flow rate of about 150 cm$^3$/min, maintaining the sample at the said temperature for 1 hour and then cooling to room temperature to produce an activated carbon gel.

In some examples of the processes described herein, the carbon nanotubes are characterized by X-ray diffraction pattern comprising peaks at one or more, or all of 26°, 42° and 53.8° degrees 2θ.

In some examples of the processes described herein, the carbon nanotubes are characterized by Raman spectra shifts of 1314 cm$^{-1}$ (D band), 1576 cm$^{-1}$ (G band), and 2625 cm$^{-1}$ (G' band).

In some examples of the processes described herein, the carbon nanotubes are characterized by Raman spectra shifts of 1314 cm$^{-1}$ (D band) of intensity $I_D$, 1576 cm$^{-1}$ (G band) of intensity $I_G$, and 2625 cm$^{-1}$ (G' band), and wherein the carbon nanotubes in contact with carbon nanospheres are characterized by $I_D/I_G$ ratios of 0.48, 1.25, 0.50, 0.52 and 1.00 for the MWCNTs, RFA-CNs, 0D, 185D and 415D samples, respectively.

Also provided herein is a carbon nanotube in contact with carbon nanospheres prepared by any process described above and herein.

Further provided herein is a composition comprising carbon nanotubes in contact with carbon nanospheres described herein.

In an instance, provided herein is a composition comprising carbon nanotubes in contact with carbon nanospheres where the carbon nanotubes in contact with carbon nanospheres are prepared by any process described above and in the Examples section.

In a specific instance, the carbon nanospheres are resorcinol-formaldehyde aerogel carbon nanospheres prepared by a process described above and in the Examples section.

In an instance, for the compositions described herein, the carbon nanotubes are characterized by Raman spectra shifts of 1314 cm$^{-1}$ (D band) of intensity $I_D$, 1576 cm$^{-1}$ (G band) of intensity $I_G$, and 2625 cm$^{-1}$ (G' band), and wherein the carbon nanotubes in contact with an aerogel carbon nanosphere are characterized by $I_D/I_G$ ratios of 0.48, 1.25, 0.50, 0.52 and 1.00 for the MWCNTs, RFA-CNs, 0D, 185D and 415D samples, respectively.

Provided herein is a catalyst comprising the composition comprising carbon nanotubes in contact with carbon nanospheres.

Also provided herein is a drug delivery agent comprising the composition comprising carbon nanotubes in contact with carbon nanospheres.

In some embodiments, provided herein are drug delivery devices. For example, set forth herein are uploaded drugs with MWCNTs/RFA-CNs, coated MWCNTs/RFA-CNs onto drugs, and mixed drugs with MWCNTs/RFA-CNs.

In some embodiments, provided herein are compositions useful for gene transfer or electrochemical analysis. For example, in some embodiments, set forth herein is a sensor that combines nucleic acid layers with electrochemical transducers to produce a biosensor for simple, accurate and inexpensive patient diagnosis. Examples include but are not limited to nanoparticle-based electrochemistry amplification, direct of DNA electrochemistry. See also T. Gregory Drummond, Michael G. Hill, Jacqueline K Barton. Electrochemical DNA Sensors. Nature Biotechnology, volume 21, pages 1192-1199 (2003), the entire contents of which are herein incorporated by reference in their entirety for all purposes.

Further provided herein is a transparent conducting film comprising the composition comprising carbon nanotubes in contact with aerogel carbon nanospheres.

In one instance, described herein is a method for water purification, the method comprising contacting water with a composition comprising carbon nanotubes in contact with carbon nanospheres.

In another instance, provided herein is a method for gene transfer or electrochemical analysis comprising the use of a composition comprising carbon nanotubes in contact with carbon nanospheres.

FIG. 1 shows the crystalline properties of MWCNTs in contact with (or decorated with) RFA-CNs via XRD. It is observed that the crystallinity of MWCNTs decreases by increasing the time for the decoration process. The characteristic peaks of MWCNTs are at 2θ=26°, 42° and 53.8°, which correspond to (002), (100) and (004) reflections of the MWCNTs, respectively. The peak noticed at 26°, which refers to (002) diffractions of graphite, exists in all samples. This confirms that the hexagonal graphite structure of the CNTs is intact in all samples. The peaks at 2θ=42.4° and 53.8° refer to an in-plane graphitic structure. Further, the intensities of the (002) diffraction in the samples 0D, 185D and 415D are 7774, 3229 and 1596, respectively. Hence, the intensity of the (002) diffraction of 185D represents 41.53% of that of 0D and the intensity of 415D represents 20.52% of that of 0D.

Figure 2:
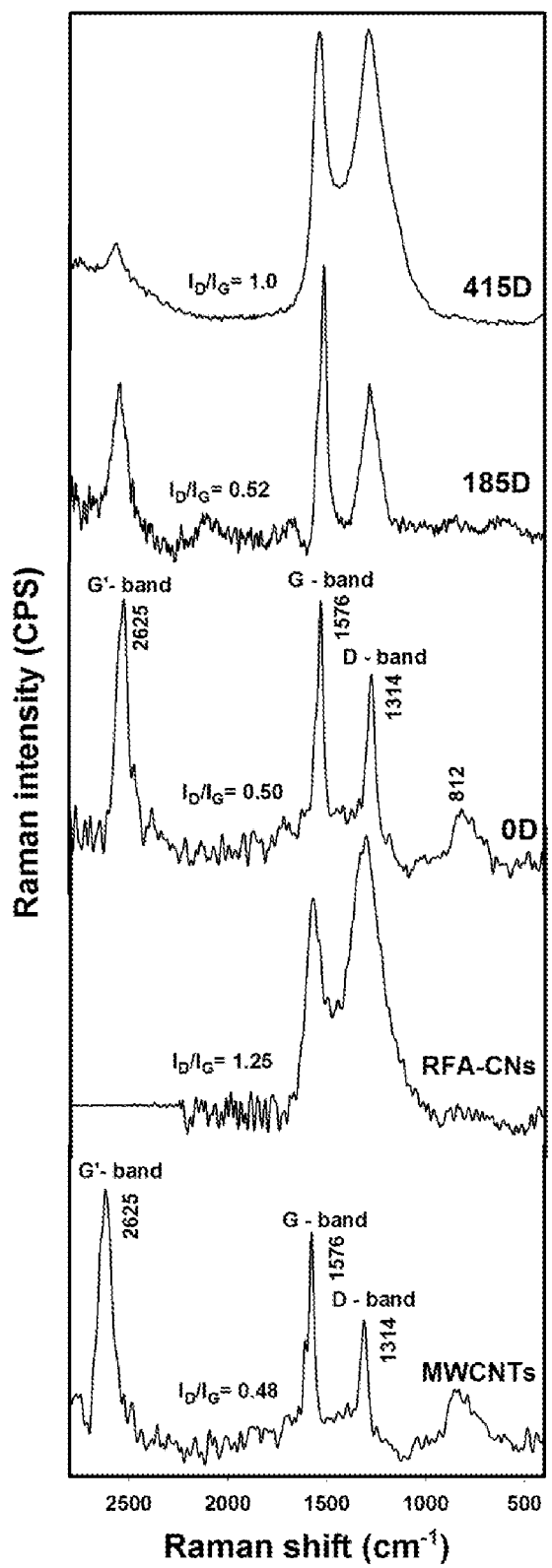
FIG. 2 shows the Raman spectra of pristine MWCNTs, pristine RFA-CNs, and the hybrid MWCNTs/RFA-CNs decorated at different times for the decoration process (i.e., samples at time zero days (0D), 185 days (185D) and 415 days (415D).

FIG. 2 shows the Raman spectra of pristine MWCNTs, pristine RFA-CNs, and the hybrid MWCNTs/RFA-CNs at different times for the decoration process (i.e., samples 0D, 185D and 415D). Raman spectra can be used to determine the degree of defects or disorders of MWCNTs after decoration with RFA-CNs. Three characteristic bands of pristine MWCNTs can be noticed as the D-band at 1314 cm$^{-1}$, G-band at 1576 cm$^{-1}$ and G'-band at 2625 cm$^{-1}$. The intensity of the D band ($I_D$) refers to disordered or amorphous carbon regions, while that of the G band ($I_G$) refers to graphite or ordered carbon regions in the MWCNTs, and that of the G' band refers to a second harmonic of the D line. Moreover, the relative disorder or defects can be evaluated by the $I_D/I_G$ ratio. The values of $I_D/I_G$ ratio are 0.48, 1.25, 0.50, 0.52 and 1.00 for the MWCNTs, RFA-CNs, 0D, 185D and 415D samples, respectively. Therefore, the degree of crystallinity of decorated CNTs decreases when the (time of the decoration process with CNs is increased.

Figure 3:
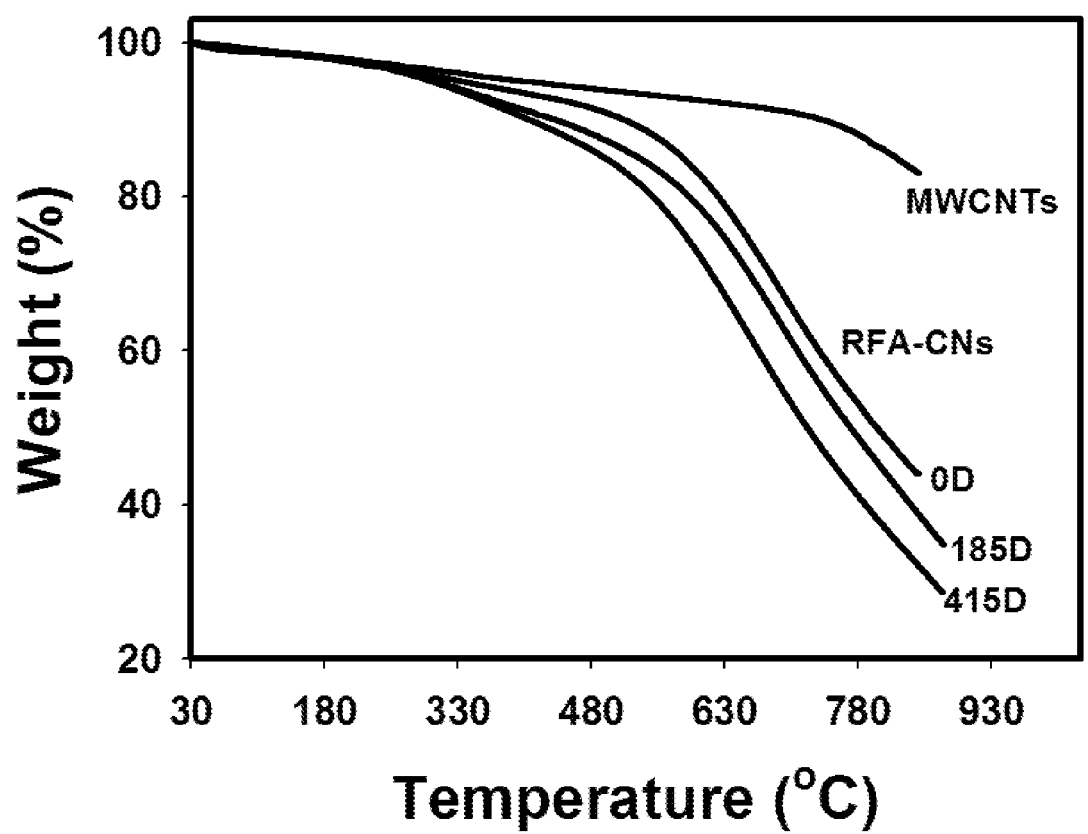
FIG. 3 shows the TGA thermograms of pristine MWCNTs, pristine RFA-CNs, and MWCNTs/RFA-CNs produced at different reaction times for the decoration process (i.e., samples 0D, 185D and 415D).

FIG. 3 shows the TGA thermograms of pristine MWCNTs, pristine RFA-CNs, and hybrid MWCNTs/RFA-CNs produced at different times for the decoration process (i.e., samples 0D, 185D and 415D). It was observed that by increasing the decoration process times, the thermal stability of MWCNTs decreases. For example, the data in Table 1, Example 3, shows that at various temperatures, the stability of samples is always in the order MWCNTs>RFA-CNs=0D>185D>415D. Consequently, the presence of RFA-CNs in contact with MWCNTs affects the samples' thermal stability. It is noteworthy to mention that the curve of RFA-CNs is overlaid on the curve of 0D. Some of the thermal decompositions of samples compared to pristine samples of MWCNTs and RFA-CNs are listed in Table 1.

Figure 4:
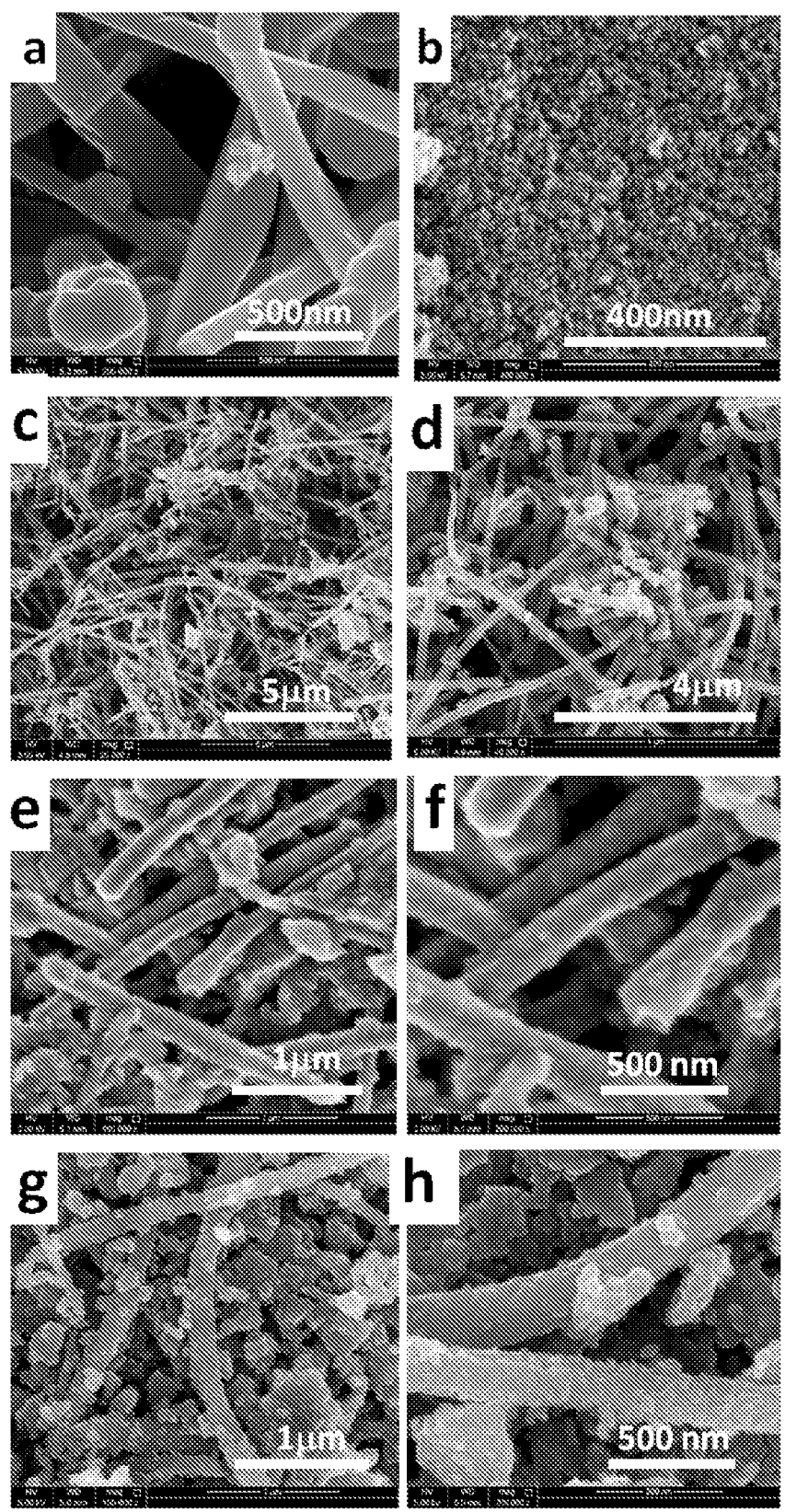
FIG. 4 (a, b) shows scanning electron microscopy (SEM) images of MWCNTs and RFA-CNs samples, respectively.

FIG. 4 (a, b) shows NanoSEM photomicrographs of MWCNTs and RFA-CNs samples, respectively. FIG. 4 (c-h) shows NanoSEM photomicrographs of MWCNTs/RFA-CNs at different decoration process times (i.e., 0D, 185D and 415D). FIG. 4a illustrates the tubular shape morphology of MWCNTs whereas FIG. 4b illustrates the spherical shape morphology of RFA-CNs. FIG. 4(c, d) exhibits two amplifications of NanoSEM photomicrographs of the MWCNTs/RFA-CNs sample "0D". It can be seen that the morphology MWCNTs is intact and that of RFA-CNs is also intact. FIG. 4(e, f) illustrates the two NanoSEM photomicrograph amplifications of the hybrid MWCNTs/RFA-CNs sample "185D". It can be noticed from FIG. 4 (e, f) that a change appeared on the outer surface of MWCNTs, as they are decorated with RFA-CNs. FIG. 4(g, h) shows two NanoSEM photomicrographs amplifications of hybrid MWCNTs/RFA-CNs for the sample "415D". It can be observed that the RFA-CNs layer on the MWCNTs grows densely and abundantly. The data shows that the hybrid carbon product has new features which are different from the starting components.

Figure 5:
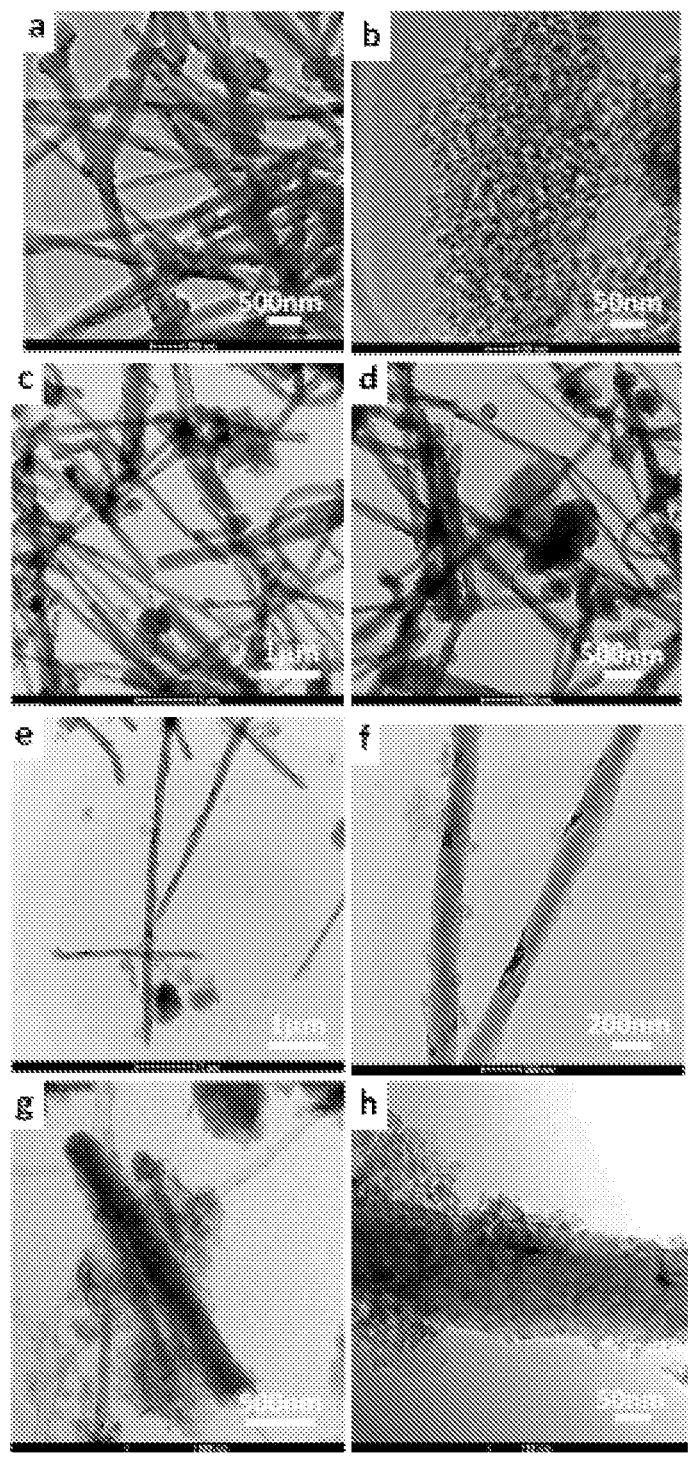
FIG. 5(a, b) shows transmission electron microscopy (TEM) images of pristine MWCNTs and RFA-CNs samples, respectively.

FIG. 5(a, b) shows TEM photomicrographs of pristine MWCNTs and RFA-CNs samples, respectively. The morphological shapes of pristine MWCNTs and RFA-CNs are tubular and spherical shapes, respectively. FIG. 5(c-h) shows TEM photomicrographs of hybrid MWCNTs/RFA-CNs at different decoration process times; 0D, 185D and 415D. FIG. 5(c, d) exposes the MWCNTs/RFA-CNs of 0D at two magnifications; 1 μm and 500 nm, respectively. It is noticed from both magnifications that the morphologies of each of the MWCNTs and RFA-CNs is intact. FIG. 5(e, f) shows the MWCNTs/RFA-CNs sample of 185D at two magnifications; 1 μm and 500 nm, respectively and shows that the morphology of NWCNTs is decorated with RFA-CNs. FIG. 5(g, h) illustrates the MWCNTs/RFA-CNs sample of 415D at two magnifications; 1 μm and 500 nm, respectively. It can be observed from both photos that the MWCNTs are decorated densely and abundantly with RFA-CNs.

Contemplated uses for the carbon nanotubes in contact with carbon nanospheres described herein (e.g., MWCNTs/RFA-CNs described herein) could include and are not limited to alcohol detection (e.g., ethanol gas sensors), modification of mechanical, electrical, thermal and chemical properties, field effect transistors, laser components, energy storage materials and biotechnology applications, elastomer application, lithium-sulfur batteries, biosensor, antioxidant, membranes, super hydrophobicity and corrosion resistance, esterification of acetic acid with methanol, dyes removal, paint applications, self-imaging applications, antimicrobial materials, carbon dioxide sensors, supercapacitor electrodes, printing process, DNA sensors, humidity sensing, removal of antibiotics, polymer actuator, anti-cancer treatments, lubricant additives, adsorption of proteins, shape-memory composites, supercapacitors, hydrogen storage, gas adsorption, adsorption of organic compounds, photosensitization, catalytic applications, sensors for aromatics, thermal insulation materials, biomedical applications, removal of organic solvents/oils, methane storage, emulsion separation, artificial neural network, proton exchange membrane fuel cells, sodium-ion batteries, solar steam generation, pulmonary delivery, solar thermal receivers, molecular sieves, photovoltaics, $H_2O_2$ sensing, electromagnetic interference shielding, strain sensors, direct methanol microfluidic fuel cell, water purification, microwave absorption, building retrofits, removal of heavy metal ions, and the like.

EXAMPLES

FT-Raman spectra were measured by a Bruker FT-Raman spectrometer of type RFS 100/S that is attached to a Bruker-IFS 66/S spectrometer, which provides high resolution to better than 0.10 $cm^{-1}$, and high sensitivity and stability. The diode-pumped, air-cooled Nd:YAG laser source with maximum laser power of 1500 mW at 1064 nm is controlled with full automation. The standard RFS 100/S configuration provides a spectral range of 70-3600 $cm^{-1}$ (Stokes shift) and 100 to 2000 $cm^{-1}$ (anti-Stokes shift).

The morphology of carbon materials were observed with a FEI Nova™ nanoscanning electron microscope 450 (Nova NanoSEM).

Transmission electron microscopy of (TEM) was conducted with a FEI Tecnai G2 F20 FE-TEM.

Thermogravimetric analyses (TGA) were carried out using a Perkin Elmer Pyris6 TGA analyzer under a flow of $N_2$ gas in range of 30° C. to 800° C. with a heating rate of 10° C./min.

X-ray diffraction (XRD) measurements were conducted by Miniflex II Benchtop XRD apparatus, manufactured by Rigaku Corporation Japan. The 2θ scan data were collected at 0.05° intervals over the range of 5 to 90°, and at a scan speed of 0.05°/min. XRD Cu k alpha.

Example 1

Synthesis of Aerogels

Aerogels were prepared from resorcinol and formaldehyde in presence of $Na_2CO_3$, which was used as catalyst. The pH of the starting solution was adjusted to a neutral value (pH ~7) with $HNO_3$ and $NH_4OH$. The quantities of resorcinol (R), $Na_2CO_3$ catalyst (C), formaldehyde (F), and water (W) that were utilized in the preparation of the aerogel were 12.44 gram, 0.0240 gram, 17.40 ml, and 32.60 ml, respectively. These quantities correspond to the molar ratios of R:F=0.5 R:C=500, and R:W=0.05 at pH 7. The medium reaction temperature was fixed at 70±1° C. Resorcinol and $Na_2CO_3$ were weighed and mixed with $H_2O$ in Erlenmeyer flasks, and the solution was stirred magnetically until the resorcinol and $Na_2CO_3$ are fully dissolved. Then, formaldehyde was added to the solution while stirring. After that, the pH value was adjusted at ~7 by using $HNO_3$ and $NH_4OH$ solutions. The RF solution was then transferred into polypropylene vials, sealed, and placed in an oven at 70±1° C. for 7 days. To prohibit the dehydration of the gel formed, and to improve their crosslinking density, 2% of $CH_3COOH$ solution was added onto the gel surface upon its solidification. After 7 days, the polypropylene vials are transferred from the oven and let to cool down to room temperature. The excess solution on top of the formed gel was decanted and disposed. The remaining (wetting) solution was solvent exchanged with acetone at ambient temperature by casting acetone on top of the sample and keeping it at ambient temperature for 24 h, and then replacing the remaining acetone with fresh acetone daily for 3 days. After the third day of solvent exchange, the samples were dried by super-critical carbon dioxide extraction. This process was carried out by multiple steps; after the cured gel was placed in the dryer, liquid carbon dioxide was introduced at a pressure of 5 MPa and a temperature of 20° C. to replace the acetone within the gel structure. The exit valve was opened and the extractor was depressurized to 1.2 MPa, letting the liquid carbon dioxide flow through the gel at 20° C. for a time ranging from 60 to 150 min. Then, the temperature was increased to approach the supercritical state of $CO_2$ at 25° C. and 5 MPa. This supercritical state was maintained for 120 min. After that, the extractor was depressurized slowly to atmospheric pressure and the dried resorcinol/formaldehyde aerogel was retrieved. The supercritical drying was conducted by using a critical point dryer (E3100 Critical Point Dryer, Quorum Technologies—Preparation for Excellence, UK).

Example 2

Carbonization and Activation of Carbon Aerogels

The dried resorcinol/formaldehyde aerogel was placed in a ceramic boat crucible into a programmable electric-heated tube furnace (Nabertherm GmbH, Germany), with a continuous flow of $N_2$ gas (100 $cm^3$/min). The furnace was first maintained at room temperature for 30 min to ensure that air is fully purged with the flowing $N_2$ gas. Afterwards, the furnace was heated up to a temperature of 500° C. with a heating rate of 10° C./min, was maintained at 500° C. for 180 min, and then allowed to cool down spontaneously to ambient temperature while flowing $N_2$ gas. The resulting RF carbon aerogel was then activated in the same tube furnace (after cleaning it thoroughly) by switching the $N_2$ gas with carbon dioxide gas flow (150 $cm^3$/min), heating the sample again at a rate of 10° C./min up to 700° C., maintaining the sample at this temperature for 60 min, and letting the sample to cool down spontaneously to room temperature while flowing the carbon dioxide gas. The outcome sample is redeemed to be an activated carbon aerogel and is called resorcinol-formaldehyde aerogel activated carbon nanospheres, which are denoted hereafter as RFA-CNs.

Example 3

Synthesis of Carbon Nanosphere-Decorated Carbon Nanotubes

The MWCNTs and RFA-CNs were mixed in a fixed weight proportion of 1:1 in reflux with methanol while stirring for 0 (0D), 185 (185D) and 415 (415D) days at 100°

Figure 6:
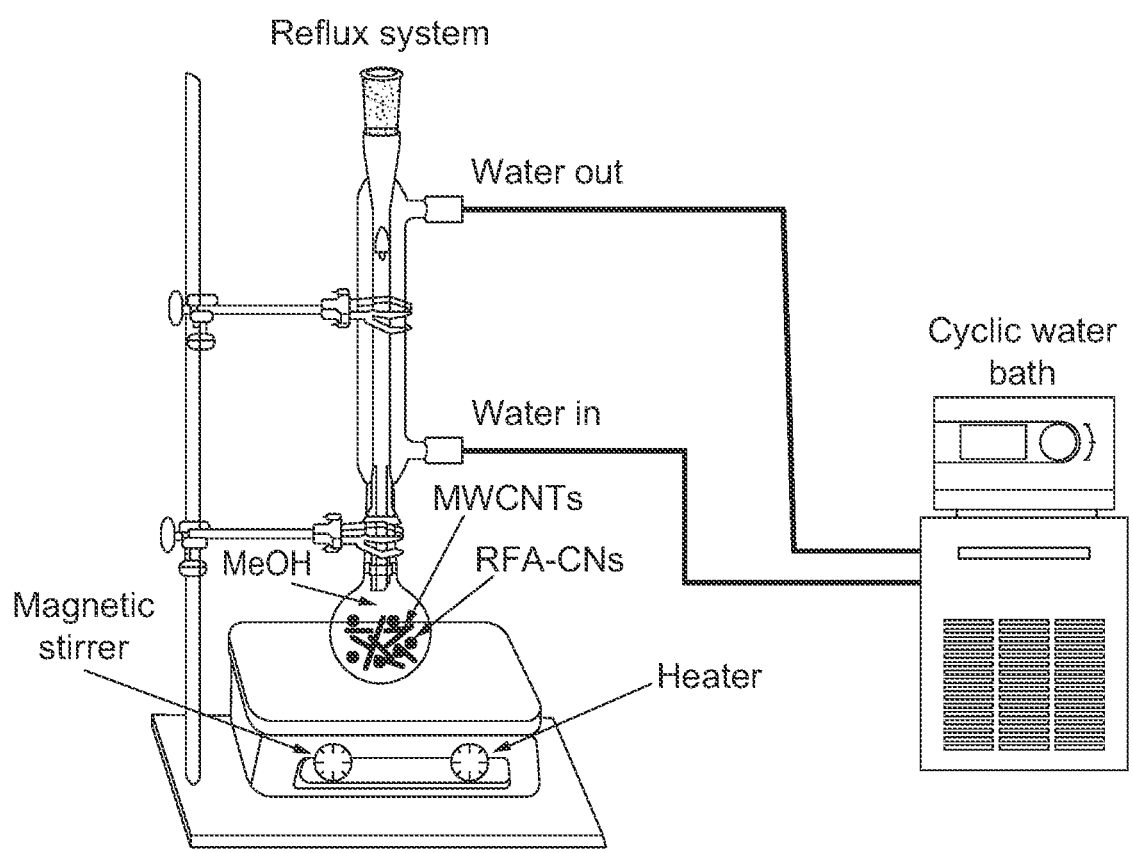
FIG. 6 is a schematic diagram for an experimental set up for the preparation of multiwalled carbon nanotubes (MWCNTs) decorated with resorcinol formaldehyde aerogel carbon nanospheres (RFA-CNs).

C. The time "0 day" refers to mixing the samples manually in dry state. The identity of these samples will be called hereafter; 0D, 185D and 415D, respectively. Samples are then dried at 110° C. for 3 days. FIG. 6 shows a schematic of the experimental setup.

Table 1 below shows the Thermogravimetric analysis (TGA) weight losses of the hybrid MWCNTs/RFA-CNs at 0 days, 185 days, and 415 days of reaction time, at different temperatures, compared to MWCNTs and RFA-CNs.

TABLE 1

Weight losses of samples at different temperatures

| Sample | Weight loss (%) | | | |
|---|---|---|---|---|
| | 353° C. | 484° C. | 678° C. | 842° C. |
| MWCNTs | 3.81 | 5.78 | 8.23 | 16.51 |
| RFA-CNs | 5.11 | 8.67 | 29.17 | 55.52 |
| 0 D | 5.11 | 8.67 | 29.17 | 55.52 |
| 185 D | 6.56 | 11.93 | 34.23 | 61.71 |
| 415 D | 7.38 | 13.73 | 42.69 | 69.02 |

FIG. 1 shows the characteristics of pristine MWCNTs, pristine RFA-CNs, and the hybrid MWCNTs/RFA-CNs decorated with at different decoration process times (i.e., samples 0D, 185D and 415D) via X-ray diffraction (XRD). FIG. 2 shows the Raman spectra of pristine MWCNTs, pristine RFA-CNs, and the hybrid MWCNTs/RFA-CNs decorated at different decoration process times (i.e., samples 0D, 185D and 415D). FIG. 3 shows the TGA thermograms of pristine MWCNTs, pristine RFA-CNs, and MWCNTs/RFA-CNs produced at different decoration process times (i.e., samples 0D, 185D and 415D). FIG. 4 (*a, b*) shows the NanoSEM photomicrographs of MWCNTs and RFA-CNs samples, respectively. FIG. 4 (*c-h*) shows the NanoSEM photomicrographs of MWCNTs/RFA-CNs at different decoration process times (i.e., 0D, 185D and 415D). FIG. 5(*a, b*) shows TEM photomicrographs of pristine MWCNTs and RFA-CNs samples, respectively. FIG. 5(*c-h*) shows TEM photomicrographs of hybrid MWCNTs/RFA-CNs at different decoration process times; 0D, 185D and 415D.

As can be seen from FIG. 1, the degree of crystallinity of decorated CNTs decreases as the reaction time is increased. As can be seen from FIG. 2, The values of intensity of D-band/intensity of G-band ($I_D/I_G$) are 0.48, 1.25, 0.50, 0.52 and 1.00 for the MWCNTs, RFA-CNs, 0D, 185D and 415D samples, respectively; and the degree of crystallinity of decorated CNTs decreases when increased decoration process time. As can be seen from FIG. 3, the thermal stability of MWCNTs decreases over time as the mixing process time increased. As can be seen from FIG. 4, the RFA-CNs attach onto MWCNTs densely and abundantly. As can be seen from FIG. 5, the RFA-CNs attach onto MWCNTs densely and abundantly.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A process for preparing a carbon nanotube in contact with an aerogel carbon nanosphere, the process comprising:
   (i) providing a mixture comprising aerogel carbon nanospheres and carbon nanotubes in a solvent;
   (ii) refluxing the mixture;
   (iii) removing the solvent to obtain a carbon nanotube in contact with an aerogel carbon nanosphere.

2. The process of claim 1, wherein the aerogel carbon nanosphere and the carbon nanotubes are mixed in a dry weight ratio of about 1:1 and stirred in the solvent.

3. The process of claim 1 or claim 2, wherein the solvent is an aprotic solvent.

4. The process of claim 1, wherein the solvent is methanol, ethanol, or isopropanol.

5. The process of claim 4, wherein the solvent is methanol.

6. The process of claim 1, wherein the mixture is refluxed for a period of about 0 day-415 days.

7. The process of claim 1, wherein the mixture is refluxed at a reflux temperature that is at 100° C.

8. The process of claim 1, wherein the solvent is removed for a period of about 1 day-5 days and the resulting residue is dried.

9. The process of claim 1, wherein the carbon nanotubes are multiwalled carbon nanotubes.

10. The process of claim 9, wherein the multiwalled carbon nanotubes are 5 to 9 μm in length.

11. The process of claim 9, wherein the multiwalled carbon nanotube diameter ranges from 110-170 nm.

12. The process of claim 1, wherein the aerogel carbon nanosphere is a resorcinol-formaldehyde aerogel carbon nanosphere.

13. The process of claim 12, wherein the resorcinol-formaldehyde aerogel carbon nanosphere is prepared by a process comprising carbonizing and activating resorcinol-formaldehyde aerogels.

14. The process of claim 13, wherein the resorcinol-formaldehyde aerogel is prepared by a process comprising:
   (i) providing a mixture comprising resorcinol, a catalyst, formaldehyde, and water;
   (ii) flu adjusting the pH to about 7;
   (iii) heating the mixture in sealed vials to about 70° C.;
   (iv) iv adding acetic acid to the mixture; and
   (v) heating the sealed vials for about 7 days.

15. The process of claim 14, wherein the vials are propylene vials.

16. The process of claim 14, wherein the acetic acid is 2% acetic acid.

17. The process of claim 14, wherein the catalyst is sodium carbonate, potassium carbonate, or cesium carbonate.

18. The process of claim 17, wherein the catalyst is sodium carbonate.

19. The process of claim 14, wherein adjusting the pH to about 7 comprises adding an acid and/or a base.

20. The process of claim 14, wherein adjusting the pH to about 7 comprises adding nitric acid and/or ammonium hydroxide.

21. The process of claim 14, further comprising the steps of
   (vi) decanting any excess solution in the vial which is on top of the resorcinol-formaldehyde aerogel; and
   (vii) solvent exchanging with an organic solvent at room temperature for about 24 hours to produce a cured gel.

22. The process of claim 21, further comprising solvent exchanging with an organic solvent at room temperature twice over 3 days.

23. The process of claim 21, wherein the organic solvent is an aprotic water miscible solvent.

24. The process of claim 21, wherein the organic solvent is acetone or tetrahydrofuran.

25. The process of claim 24, wherein the organic solvent is acetone.

26. The process of claim 22, further comprising the step of flowing liquid or supercritical carbon dioxide through the cured gel.

27. The process of claim 26, wherein flowing liquid or supercritical carbon dioxide through the cured gel occurs in an extractor at a pressure of about 5 MPa and a temperature of about 20° C.

28. The process of claim 27, further comprising depressurizing the extractor to about 1.2 MPa.

29. The process of claim 28, wherein, after depressurizing, the process further comprises flowing carbon dioxide through the gel at 20° C. for a time ranging from about 1 to 3 hours to afford a dried resorcinol-formaldehyde aerogel.

30. The process of claim 29, further comprising carbonizing and activating the dried resorcinol-formaldehyde aerogel, wherein carbonizing and activating comprises the steps of:
 (viii) heating the resorcinol-formaldehyde aerogel for a period of at least 1 hour; and
 (ix) cooling the resorcinol-formaldehyde aerogel to room temperature under carbon dioxide gas.

31. The process of claim 30, comprising heating the resorcinol-formaldehyde aerogel at a rate of 10° C./min up to a temperature of 700° C. in an atmosphere of carbon dioxide flowing at a rate of about 150 cm³/min.

32. The process of claim 1, wherein the carbon nanotubes are characterized by X-ray diffraction pattern comprising peaks at one or more, or all of 26°, 42° and 53.8° 2θ.

33. The process of claim 1, wherein the carbon nanotubes are characterized by Raman spectra shifts of 1314 cm⁻¹, 1576 cm⁻¹, and 2625 cm⁻¹.

34. The process of claim 1, wherein the carbon nanotubes are characterized by Raman spectra shifts of 1314 cm⁻¹ of intensity $I_D$, 1576 cm⁻¹ (G band) of intensity $I_G$, and 2625 cm⁻¹ (G' band), and wherein the carbon nanotubes in contact with the aerogel carbon nanosphere are characterized by an $I_D/I_G$ ratio of 1 after day 415.

35. A carbon nanotube in contact with aerogel carbon nanospheres.

36. A composition comprising carbon nanotubes in contact with aerogel carbon nanospheres.

37. The composition of claim 36, wherein the carbon nanotubes in contact with aerogel carbon nanospheres are prepared by a process comprising:
 (i) providing a mixture comprising aerogel carbon nanospheres and carbon nanotubes in a solvent;
 (ii) refluxing the mixture;
 (iii) removing the solvent to obtain a carbon nanotube in contact with an aerogel carbon nanosphere.

38. The composition of claim 37, wherein the aerogel carbon nanospheres are resorcinol-formaldehyde aerogel carbon nanospheres and wherein the resorcinol-formaldehyde aerogel carbon nanospheres are prepared by a process comprising:
 (i) providing a mixture comprising resorcinol, a catalyst, formaldehyde, and water;
 (ii) adjusting the pH to about 7;
 (iii) heating the mixture in sealed vials to about 70° C.;
 (iv) adding acetic acid to the mixture; and
 (v) heating the sealed vials for about 7 days.

39. The composition of claim 38, wherein the carbon nanotubes are characterized by Raman spectra shifts of 1314 cm⁻¹ (D band) of intensity $I_D$, 1576 cm⁻¹ (G band) of intensity $I_G$, and 2625 cm⁻¹ (G' band), and wherein the carbon nanotubes in contact with the aerogel carbon nanosphere are characterized by an $I_D/I_G$ ratio of 1 for the sample decorated after day 415.

40. A catalyst comprising the composition of claim 37.

41. A drug delivery agent comprising the composition of claim 37.

42. A transparent conducting film comprising the composition of claim 37.

43. A method for water purification, the method comprising contacting water with a composition of claim 37.

* * * * *